United States Patent [19]

Manchak, Jr.

[11] Patent Number: 4,844,807

[45] Date of Patent: Jul. 4, 1989

[54] INSITU HAZARDOUS WASTE TREATING APPARATUS AND METHOD OF USING SAME

[76] Inventor: Frank Manchak, Jr., 124 Santa Felecia Dr., Goleta, Calif. 93117-2804

[21] Appl. No.: 49,861

[22] PCT Filed: Aug. 4, 1986

[86] PCT No.: PCT/US86/01638

§ 371 Date: Apr. 22, 1987

§ 102(e) Date: Apr. 22, 1987

[87] PCT Pub. No.: WO87/01312

PCT Pub. Date: Mar. 12, 1987

Related U.S. Application Data

[63] Continuation of PCT/US85/01656, filed Aug. 26, 1985, which is a continuation-in part of 646,745, Sept. 4, 1984, abandoned.

[51] Int. Cl.⁴ .............................................. B01D 17/12
[52] U.S. Cl. ................................. 210/682; 210/747; 210/751; 210/739; 210/96.1; 210/170; 210/188; 405/128; 405/263; 175/50; 252/628; 252/631
[58] Field of Search .............. 210/180, 188, 681, 682, 210/170, 747, 198.1, 205, 209, 219, 714, 751, 712, 96.1, 739; 405/128, 129, 233, 258, 263, 269, 266, 53, 270, 268; 208/13, 112, 120, 121; 252/628–631; 175/50

[56] References Cited

U.S. PATENT DOCUMENTS

| 4,376,598 | 3/1983 | Brouns et al. | 405/258 |
| 4,611,950 | 9/1986 | Russomano | 210/170 |
| 4,715,965 | 12/1987 | Sigerson et al. | 110/346 |
| 4,758,355 | 7/1988 | Levine | 210/747 |

OTHER PUBLICATIONS

Manchak, Insitu Waste Impoundment Treating Apparatus and Method of Using Same, Int. Pub. No. WO86/01439, 13 Mar. 86.

Primary Examiner—Richard V. Fisher
Assistant Examiner—Joseph Drodge
Attorney, Agent, or Firm—Roth & Goldman

[57] ABSTRACT

The insitu method of detoxifying a hazardous waste impoundment to a desired degree at a first station thereon without contaminating the ambient atmosphere is carried out by an apparatus (U) that includes a power operated vehicle (V) that movably supports a frame (W) that has a confined space defining shroud (X) on the lower end thereof that is in sealing contact with the impoundment during the carrying out of the method. A power driven cutter (Z) when moved downwardly below the shroud (X) forms a vertical zone A of particled hazardous waste. Pressurized steam from a boiler (B) is discharged into zone A. Volatile toxic organic compounds in zone (A) flow upwardly into shroud (X). A blower (C) withdraws air, steam, toxic vapors and toxic gases from shroud (X) as a toxic stream and at a sufficiently rapid rate as to maintain a negative pressure within the shroud, with the stream after being freed of toxic components by a unit (P) being returned to zone A. The major portion of water soluble salts of toxic metals present in zone (A) are transformed to substantially water insoluble compounds by discharging an oxidizing agent into zone (A) by use of a pump (G). When a sensing unit (F) indicates zone (A) has been detoxified to a desired degree a feeder (H) is used to discharge a dewatering agent into zone A to transform the latter to a water impermeable mass from which toxic components remaining therein will not leach out. The above described method is carried out by apparatus (U) in succession at a number of second stations to encompass the entire impoundment, define a barrier wall therearound, or a linear thereunder.

29 Claims, 9 Drawing Sheets

INSITU HAZARDOUS WASTE TREATING APPARATUS AND METHOD OF USING SAME

This application claims priority under 35 U.S.C. 120 from U.S. patent application No. 646,745, filed Sept. 4, 1984, now abandoned, and is related thereto by continuation, PCT/US85/01656 (CIP) filed Aug. 26, 1985, and PCT/US86/01638 (CIP) filed Aug. 4, 1986.

DESCRIPTION OF THE PRIOR ART

Many of the hazardous waste impoundments encountered are relatively old, and records of the identity of the toxic components therein and the location thereof in the impoundment are often incomplete or non existent. Likewise, due to the age of the impoundment the location of solid objects such as drums, barrels and tanks therein may be unknown. In such an impoundment toxic organic compounds may have reacted over a period of time to form toxic gaseous compounds of a highly objectionable odor that are under pressure and are beginning to off gas from the impoundment.

Hazardous waste impoundments as above described are a health hazard for the upper portions thereof exposed to the sun become dry and dusty and particles thereof tend to become airborne due to the action of the wind. Such air borne particles are particularly hazardous if the impoundment is one that contains radioactive material and is emitting radon gas. In addition, toxic compounds tend to leach out from the impoundment over a period of time and contaminate the water table. The same health hazard prevails when the hazardous toxic waste is stock piled on the ground surface.

Various remedial actions have been proposed and used in the past, but are unsatisfactory from a health standpoint due to either the unreliability thereof, the excavating and hauling of the hazardous waste, or the long period of time required to detoxify the impoundment by land farming which is accomplished by the use of micro-organisms.

A common expedient in the past has been to form downwardly extending isolation walls around the periphery of the impoundment from concrete or bentonite, but due to the concrete or bentonite being mixed with untreated soil there is no certainty that porous windows or actual openings will not form in the wall to permit toxic material from the impoundment to migrate therethrough.

Excavation and hauling is unsatisfactory in that it involves mechanical movement of the impoundment with the release of dust and toxic gases therefrom to the ambient atmosphere, and the hauling of toxic material from a first site to a second site without treatment, and with the ever present danger that it may be inadvertently spilled when being so transported. Excavation further permits out gassing of toxic fumes from the impoundment to contaminate the ambient atmosphere.

A major object of the present invention is to provide an insitu method of treating and detoxifying hazardous toxic waste that is randomly distributed over a geographical area and varies both as to the identity of the toxic components therein, the concentration thereof, and the depth they are located below the ground surface, and such treatment not contaminating the ambient atmosphere.

Another object of the insitu method of detoxifying is to provide one that is relatively rapid in carrying out, and is free of the operational disadvantages of prior art remedial actions previously described.

A further object of the insitu method of detoxifying is to supply a method that is free from the hazard of hauling toxic material over a public highway, and one that is particularly effective in treating impoundments containing radioactive material to minimize the escape of radon therefrom.

Yet another object of the insitu method of the present invention is the flexibility of the use thereof, permitting either the detoxification of the entire impoundment, the forming of a barrier wall therearound, or a liner that extends downwardly and under the impoundment.

A still further object of the invention is to provide a first form of apparatus that is movable and detoxifies a hazardous waste impoundment by carrying out the insitu detoxifying method at a succession of overlapping stations thereon.

Another object of the invention is to provide a first modified form of the detoxifying apparatus that is mounted on a base and occupies a stationary position adjacent an above ground stock pile of hazardous waste material or newly generated hazardous waste for the detoxifying of the latter.

A further object of the invention is to supply a second modified form of the detoxifying apparatus that is used to check and verify the identity and quantity of toxic components randomly distributed in a hazardous waste impoundment at selected locations on the latter and prior to the actual detoxifying of the impoundment by the insitu method of the present invention.

A still further object of the invention is to supply a first form of apparatus that while detoxifying a hazardous waste impoundment at a station thereon, is sampling the identity and quantity of the toxic components in the next station to be detoxified, and is also sampling the identity and quantity of any toxic components remaining in the station it has just detoxified.

These and other objects and advantages of the invention will become apparent from the following detailed description of the insitu method of detoxification and the apparatus used in conjunction therewith.

SUMMARY OF THE INVENTION

The insitu method of detoxifying a hazardous waste impoundment is carried out by a first form of apparatus that includes a power driven vehicle that movably and adjustable supports an elongate, vertically extending frame on one side thereof. The frame on the lower end supports an inverted, cup shaped shroud, which shroud has a lower peripheral edge portion that may be driven downwardly into the upper surface of the hazardous waste impoundment to effect a seal therewith, and the shroud and impoundment cooperating to define a confined space.

The frame supports at least one power driven vertically disposed tubular drill pipe or kelly that may be moved longitudinally relative to the frame. The kelly extends downwardly through the shroud, and on the lower end the kelly supports a cutter that includes two oppositely extending cutting blades, with one of the blades having a number of longitudinally spaced nozzles on the trailing edge thereof. The cutter also includes at least one opening through which pressurized air that may be heated and powdered material may be discharged. The shroud has a number of second nozzles therein through which jets of pressurized water may be discharged.

The insitu method of detoxifying a hazardous waste impoundment that includes soil is initiated by rotating the cutter and moving it downwardly through the impoundment to form a zone of particled material. Steam is discharged through the first nozzles as pressurized jets that impinge on the particles and reduce the size thereof. Pressurized jets of water are discharged through the second nozzles to assist the cutter in forming the zone. Continued rotation of the cutter agitates the particles in the zone.

The discharging jets of steam heat the zone and tend to displace free toxic gases therefrom that flow upwardly into the confined space. Heat from the steam jets heats the zone to the extent that toxic organic compounds volatile at the temperature of the steam being used flow upwardly into the confined space as toxic vapors.

Sensing means indicate the identity and quantity of toxic compounds present in the zone. A blower constantly removes air, steam, toxic vapors and toxic gases from the confined space at a sufficiently rapid rate as to maintain a negative pressure therein and discharges the air, steam, toxic gases and vapors as a toxic stream. The toxic gases and toxic vapors at the option of the user may be removed by cooling the toxic stream to cause condensation of at least a part thereof and removing the balance by passing the toxic stream through a quantity of activated carbon, heating the toxic stream and discharging it through a catalyst containing thermal oxidizer to transform the toxic components into non-toxic compounds, or directing the toxic stream through a plasma oven to transform toxic components to nontoxic compounds, irrespective of which of the three above-mentioned methods is used, the resulting stream of air free of toxic components is recycled back into the zone and tends to displace free toxic gases therefrom.

If the sensing unit indicates that disagreeable odor producing compounds such as certain organics, hydrogen sulphide, sulphur dioxide; water soluble salts of toxic metals; or toxic organic compounds not volatile at the temperature of the steam being used are present, a liquid oxidizing agent such as hydrogen peroxide or an aqueous solution of potassium permanganate is discharged into the zone through the first nozzles when steam is not discharging therefrom.

The oxidizing agent transforms the hydrogen sulphide and sulphur dioxide to elemental sulphur, hydrogen and oxygen, and reacts with the major portions of the water soluble salts of toxic metals to form substantially water insoluble compounds. The oxidizing agent for reasons not understood tends to transform long chain hydrocarbons not volatile at the temperature of the steam being used into shorter chain hydrocarbons that are volatile at the steam temperature and flow upwardly into the confined space as toxic vapors.

When the sensing means indicates that the zone has been detoxified to a desired degree a powdered dewatering agent is blown downwardly through the hollow kelly to discharge from the openings in the cutter, and through which pressurized streams of hot air may be discharged if desired. The dewatering agent is one that effects an ion exchange between clay in the soil and the agent, with the material in the zone being transformed to a hard, dense, water impermeable mass. The cutter is removed from the zone prior to the completion of this transformation. Water soluble salts of toxic metals that have not been transformed to substantially water insoluble compounds, long chain hydrocarbons not volatile at the temperature of the steam being used, and radon emitting radioactive compounds remain enveloped in the water impermeable mass and will not leach therefrom over a prolonged period of time. The water impermeable mass is sufficiently dense that little or no radon will escape therefrom, as the migration of radon is so slow through the mass that it will transform to a solid radioactive element prior to reaching the exterior surface of the mass.

When the detoxifying of a zone has been completed at a first station on the impoundment the apparatus is moved to a second adjacent station and the method repeated until the desired portion of the impoundment has been detoxified. In commercial use of the apparatus it is desirable that at least a pair of spaced cutters be used, and preferably two pairs to provide a zone of substantial transverse cross section.

Prior to the above described method being carried out the hazardous waste impoundment is subjected to a radar scan to find the location of barrels, drums, tanks and other solid debris. The loaction of these objects is marked on a grid map of the hazardous waste impoundment. Also, prior to the detoxifying method being carried out the hazardous waste impoundment is subjected to test bore holes to determine the identity of toxic components present therein and the depth thereof, and to permit the insitu method to be adjusted to handle the toxic components so identified. The impoundment is also subjected to the verifier from of the apparatus to obtain further information as to the toxic contamination thereof.

A stationary form of the detoxifying apparatus may be used on above ground toxic waste material such as oil well cuttings, drilling mud, paint residues, pesticides and the like, and operates substantially in the same manner as the movable form, and differs primarily from the movable form in that the toxic material is being moved into sealed communication with the shroud rather than the shroud being moved into communication with the hazardous waste impoundment.

Toxic residue resulting from the detoxifying method when refrigeration is used to cool the toxic stream may be advantageously disposed of in a plasma furnace, which furnace may also be used to regenerate used activated carbon.

BRIEF DESCRIPTION OF THE DRAWINGS

FIG. 10 is a diagrammatic view of a portion of the kelly drive mechanism;

FIG. 11 is a side elevational view of the intermediate platform moving mechanism on the assembly shown in FIG. 2;

FIG. 12 is a diagrammatic view of a plasma torch that may be supported by a kelly to transform a treated zone to a vitrified mass;

DESCRIPTION OF THE PREFERRED EMBODIMENT

Figure 1:
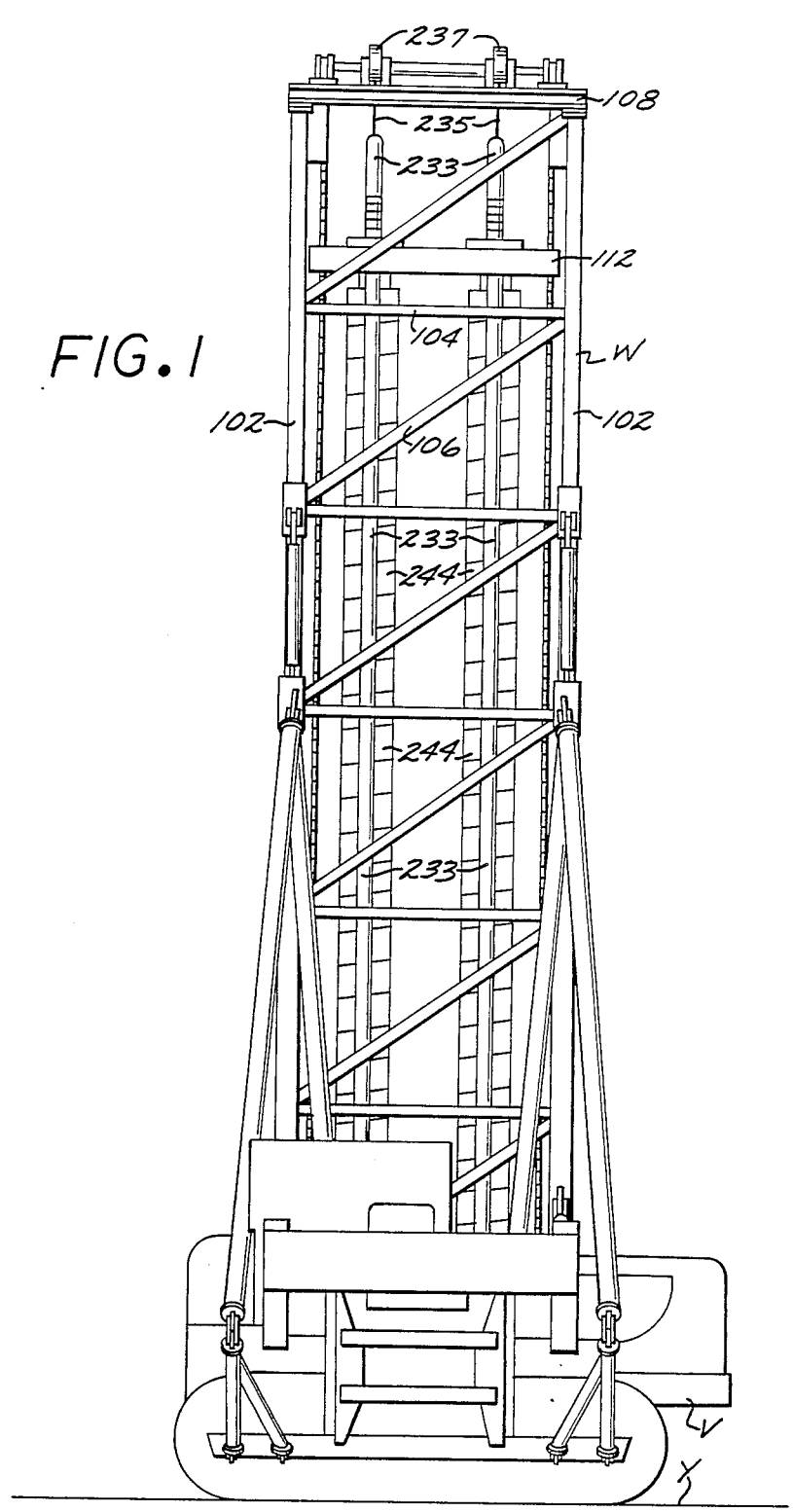
FIG. 1 is a side elevational view of a portion of a movable assembly that is used in the insitu detoxification of a hazardous toxic waste impoundment.
Figure 2:
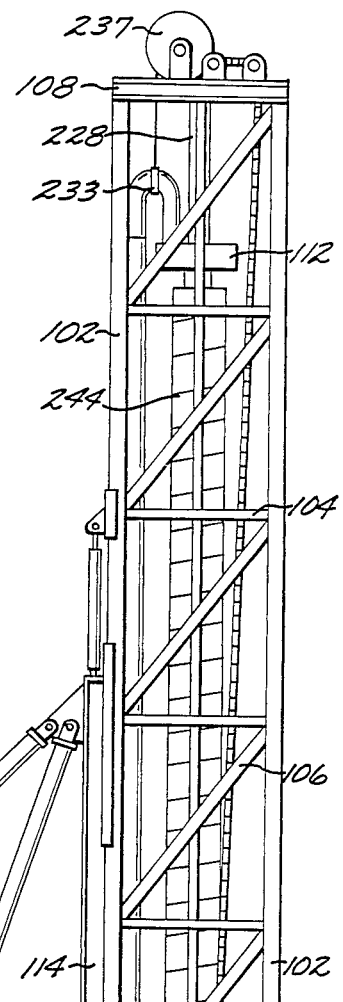
FIG. 2 is an end elevational view of the assembly shown in FIG. 1.
Figure 2:
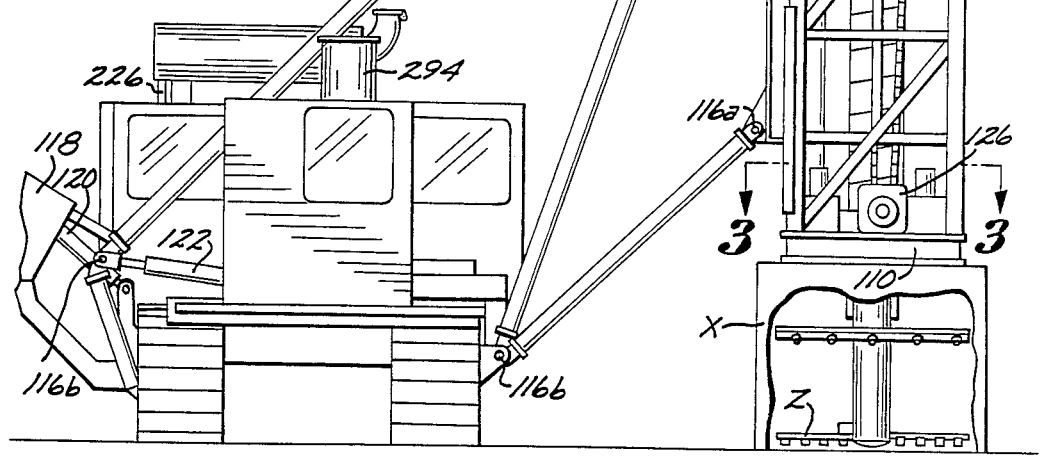
Figure 5:
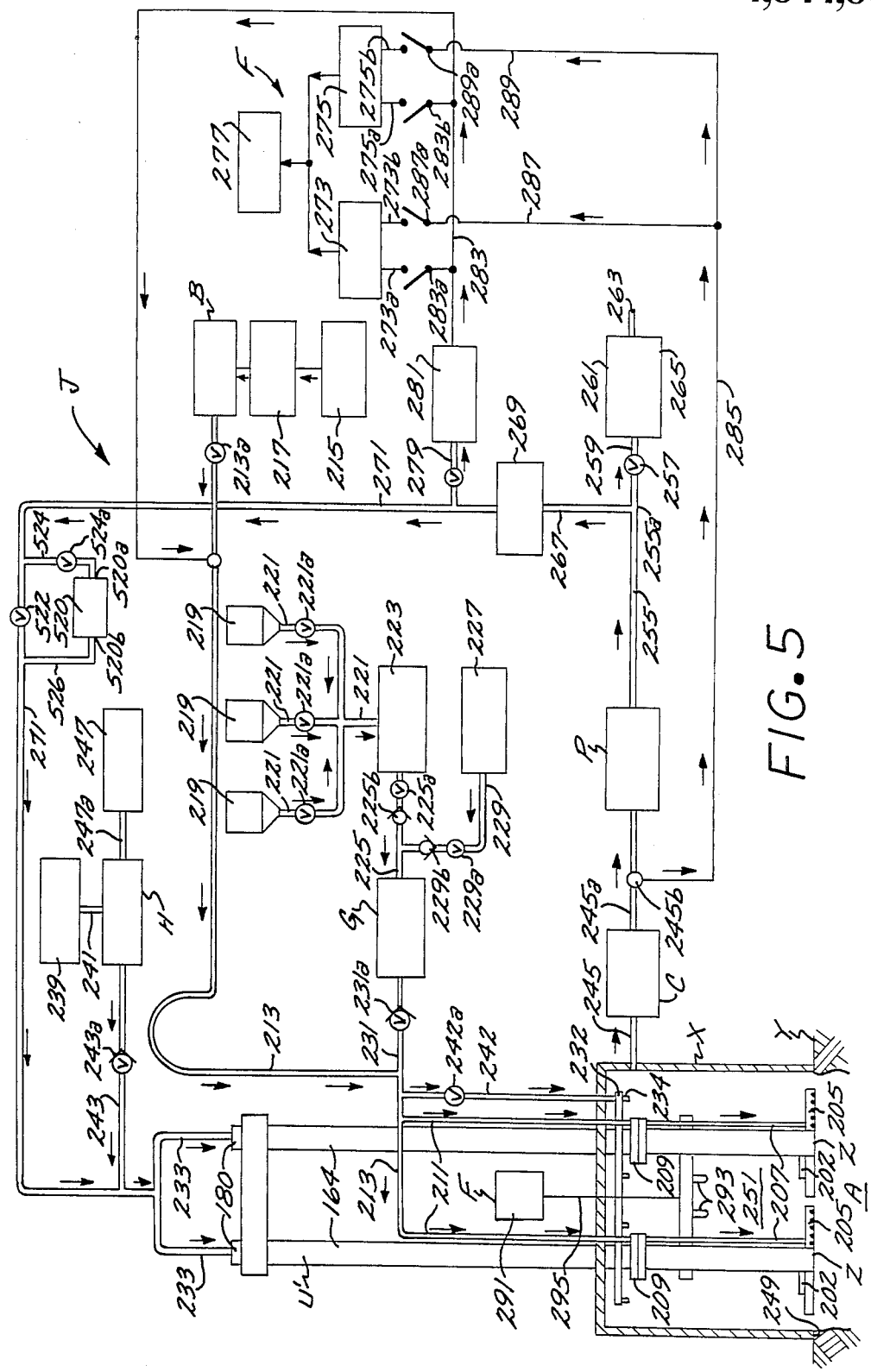
FIG. 5 is a diagrammatic view of a portion of the first form of the assembly not shown in FIGS. 1 and 2.
Figure 6:
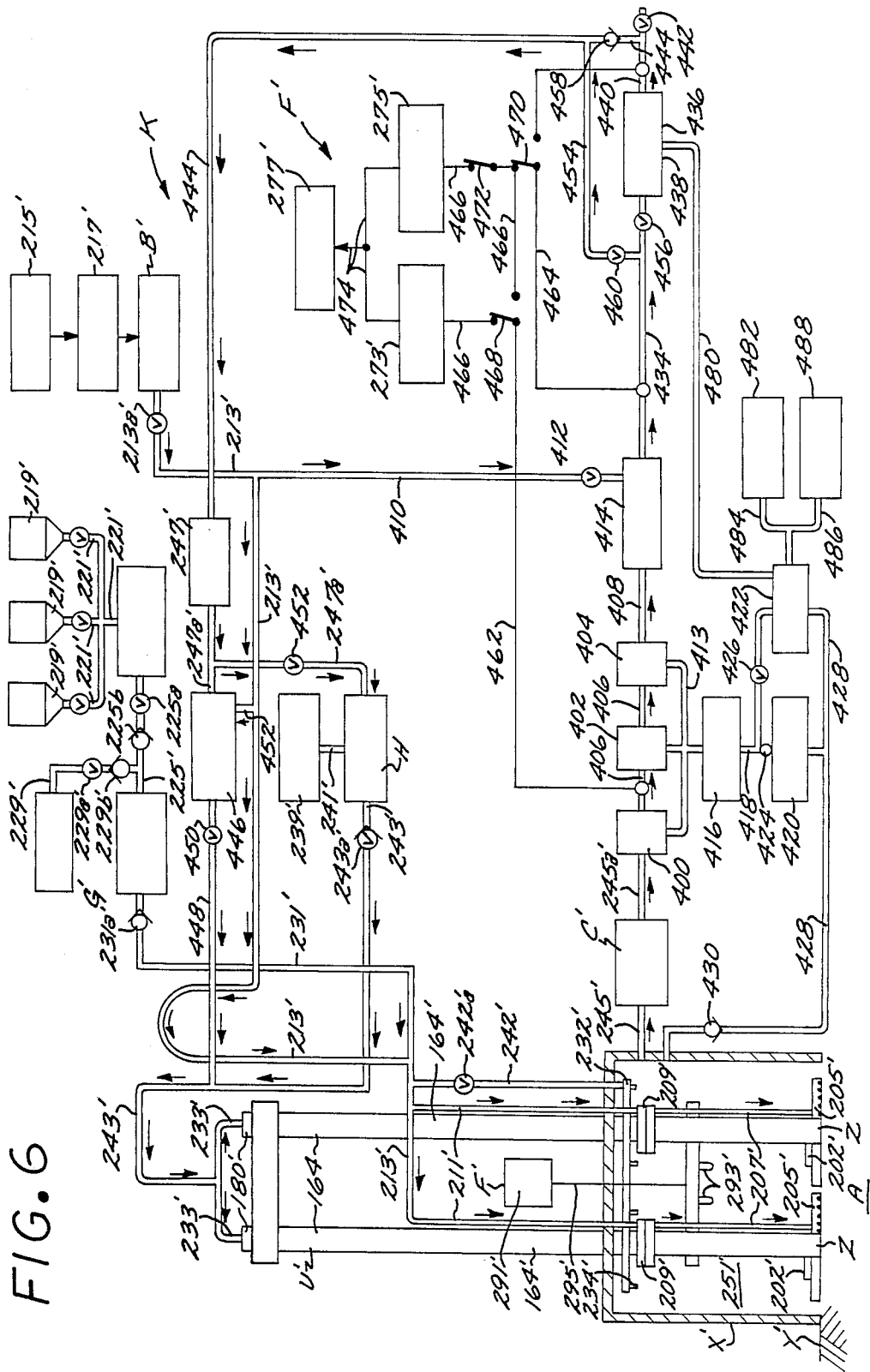
FIG. 6 is a diagrammatic view of a portion of the second form of the assembly not shown in FIGS. 1 and 2.

The detoxification of a hazardous waste impoundment Y by the insitu method of the present invention is carried out by use of the movable apparatus U illustrated in FIGS. 1 and 2 in combination with either the first or second assemblies J or K shown in FIGS. 5 and 6. The first and second assemblies J and K include those elements not illustrated in FIGS. 1 and 2.

Apparatus U includes a vertically extending frame W movably supported in an outwardly disposed from a power vehicle V, which is illustrated in FIGS. 1 and 2 as a caterpillar type tractor, and the tractor also supporting an instrumentation and control cab 100.

Frame W is illustrated as formed from four corner members 102, cross pieces 104, and reinforcing members 106. The frame W includes an upper platform 108, lower platform 110, and intermediate movable platform 112.

A support assembly 114 shown in FIG. 2 permits frame W to be moved relative to vehicle V. Support assembly 114 includes a number of elongate rigid members 116 that are secured to the frame W by pivotal connections 116a and to vehicle V by pivotal connections 116b. A counterweight 118 is by a linkage assembly 120 operatively associated with assembly 114 to balance the weight of the frame V and operating components later to be described. A first hydraulic cylinder 122 is so pivotally connected to the linkage assembly 120 and vehicle V as to permit lateral movement of the frame W relative to the vehicle when the hydraulic cylinder 122 is activated. A second hydraulic cylinder 124 is pivotally connected to support assembly 114 and frame W in such a manner as to permit relative vertical movement of the frame to the vehicle when the hydraulic cylinder 124 is activated. Hydraulic cylinders 122 and 124 are shown in FIG. 2.

Figures 10, 11, 12:
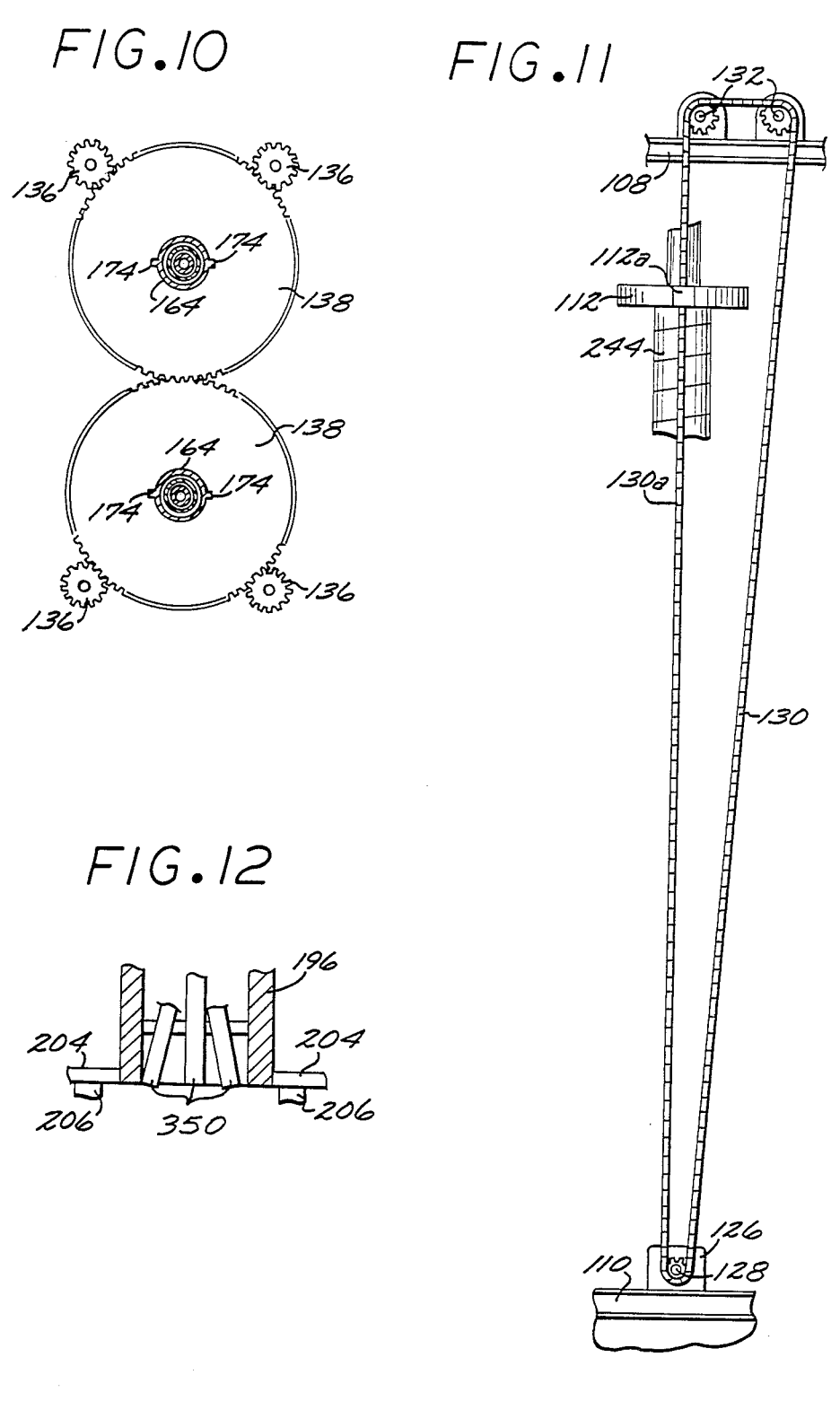

A confined space defining shroud X extends downwardly from lower platform 110 and into which shroud a power driven rotatable cutter Z is vertically Z is vertically movable. A laterally spaced pair of motors 126 are mounted on lower platform 110 and rotate drive sprockets 128 as shown in FIG. 11. Each drive sprocket 128 engages an upwardly extending endless link belt 130 that rotatably engages a pair of sprockets 132 rotatably supported from upper platform 108. Intermediate platform 112 is secured by conventional fastening means 112a to a vertical reach 130a of belt 130.

Figure 3:
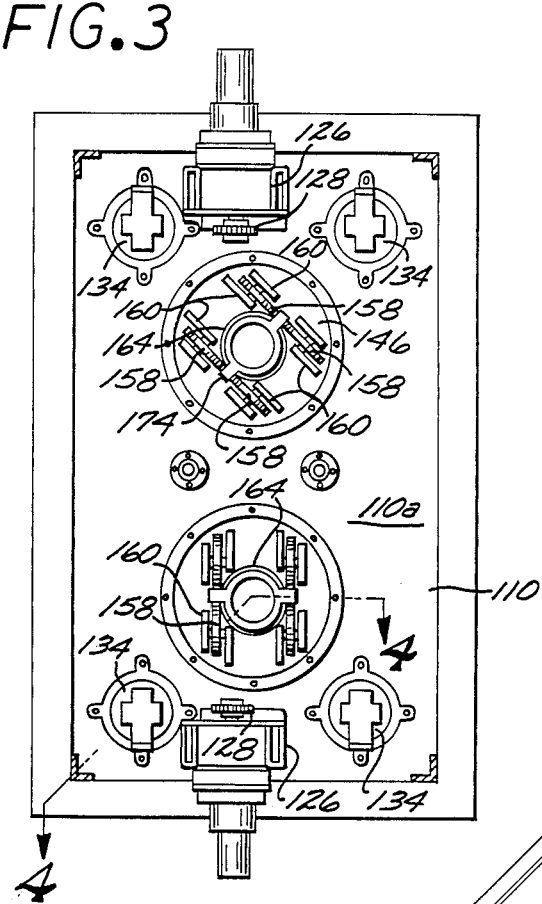
FIG. 3 is a transverse cross sectional view of the assembly shown in FIG. 2 taken on the line 3—3 thereof.

The lower platform 110 has two pairs of electric motors 134 mounted thereon that rotate driving sprockets 136 as shown in FIGS. 3 and 10 that are in toothed engagement with a pair of driven gears 138, which gears are also in toothed engagement.

Figure 4:
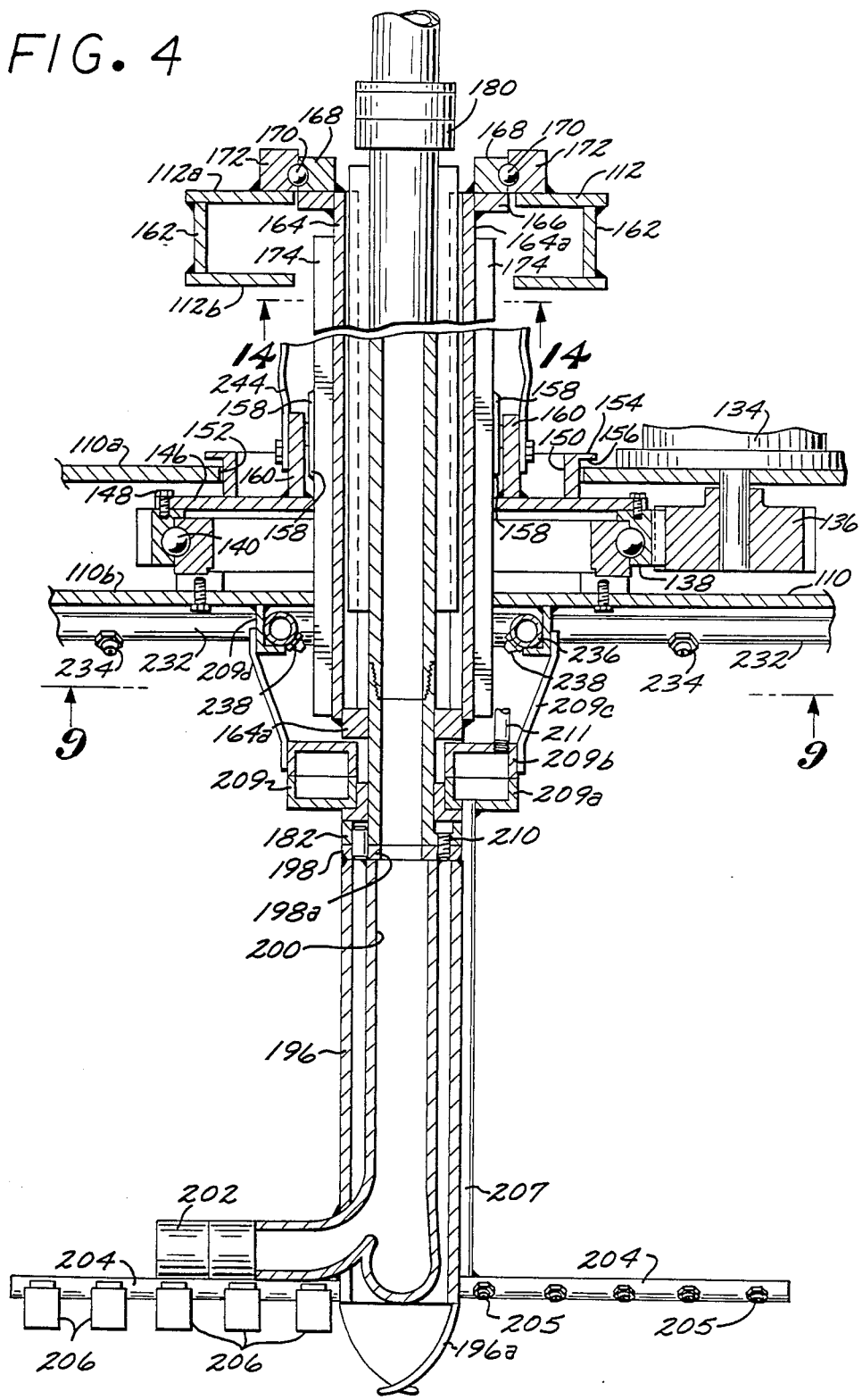
FIG. 4 is a vertical cross sectional view of the assembly shown in FIG. 3.taken on the line 4—4 thereof.

The lower platform 110 as may be seen in FIG. 4 is defined by an upper horizontal plate 110a and lower plate 110b. Each driven gear 138 is ring shaped and is rotatably supported by a sequence of ball bearings 140 from a ring shaped mounting assembly 142 that is secured to lower plate 110b by bolts 144 as shown in FIG. 4.

Each driven gear 138 has a flat rigid ring shaped member 146 secured to the upper surface thereof by bolts 148 as shown in FIG. 4. Each member 146 has a cylindrical shell 150 projecting upwardly therefrom and passing through an opening 152 in upper plate 110a. In FIG. 4 it will be seen that each shell 150 has a flange 154 projecting outwardly therefrom that supports a seal 156 in sliding contact with the upper surface of upper plate 110a.

Figure 8:
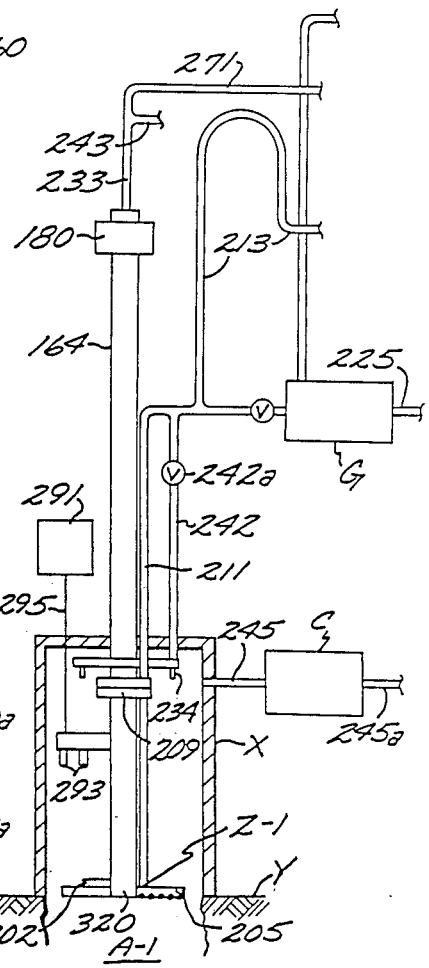
FIG. 8 is an enlarged combined transverse cross sectional and top plan view of one of the kelly drives for the assembly shown in FIGS. 1 and 2.

In FIGS. 4 and 8 it will be seen that two spaced pairs of rollers 158 are rotatably supported above upper plate 110a from lugs 160 that are secured to members 146.

The intermediate platform 112 as may be seen in FIG. 4 is defined by upper and lower vertically spaced rigid horizontal plates 112a and 112b that are joined by connectors 162. Two tubular kellys 164 used in driving cutters Z have upper portions 164a disposed within intermediate platform 112. Each portion 164a has an outwardly extending flange 166 secured thereto, which flange has an externally grooved, ring shaped, member 168 affixed secured thereto that rotatably engages a sequence of ball bearings 170. The ball bearings 170 engage an internally grooved ring shaped member 172 secured to the upper plate 112a of intermediate platform 112.

Each kelly 164 has two oppositely disposed vertically extending ribs 174 projecting outwardly from the external surface thereof as shown in FIG. 8, which ribs are rotatably engaged by the two pairs of rollers 158. Each kelly 164 has a horizontal member 164b secured to the lower end thereof that supports a centrally disposed tubular member 176 of substantially smaller diameter than that of kelly 164. Tubular member 176 serves as a mounting for a tube 178 that extends upwardly to the top of kelly 164, and is connected to a tubular swivel 180. The lower end of tubular member 176 develops into an outwardly extending flange 182.

Each cutter Z as illustrated in FIG. 4 includes an outer tube 196 that has a pointed lower end 196a and the upper end of the tube being secured to a circular plate 198 that has a centered opening 198a therein. An inner tube 200 is secured to plate 198 and is in communication with opening 198. Inner tube 200 on the lower end develops into a number of tubular discharge members 202 that extend through outer tube 196.

Two oppositely disposed cutting blades 204 extend outwardly from the lower end of outer tube 196 and support a number of spaced jets by the nozzles 234 and 238 for purposes that will later be explained. Toxic gases that arise during the detoxification of impoundment Y are prevented from escaping upwardly around kellys 164 by tubular bellows 244 that envelop the kellys. The lower end of the bellows 244 are sealingly secured to lugs 160 by conventional means and the upper ends of the bellows to the lower surface of intermediate platform 112. The apparatus above described is mounted on the vehicle V and may be used equally well with either the first form of assembly J shown in FIG. 5 or a second form of assembly K illustrated in FIG. 6. Both the first and second form of assemblies J and K are mounted on vehicles (not shown) that move concurrently with vehicle V.

Prior to using the apparatus U it is desirable than an underground radar scan be made of the hazardous waste impoundments to locate buried drums, tanks, barrels, and the like that may contain dangerous materials. Suitable precautions must be taken when detoxifying the portions of the impoundment Y adjacent thereto.

After obtaining the above information, as well as an analysis of a sample of the hazardous waste impoundment Y to obtain the composition thereof, by a verifying apparatus later to be described, the apparatus U is moved to a first station adjacent the impoundment and the frame W is moved to dispose the lower edge of shroud X which is of rigid construction in pressure sealing contact with the upper surface of impoundment Y.

The motors 134 are now caused to drive the members 146 with the rollers 158 exerting a rotational force on the ribs 174 to rotate kellys 164 and the cutter Z. Motors 126 are now energized to drive belts 130 to move intermediate platform 112 downwardly to exert a downward force on kellys 164 and cutters Z.

Operation of the apparatus U results in the cutters Z forming a downwardly extending zone A of particled hazardous waste impoundment material mixed with soil below shroud X.

When the first form of assembly J shown in FIG. 5 is used with apparatus U it will be seen that a conduit 245 extends from the upper interior of shroud X to the intake of a power driven blower C. The steam and liquid supply conduits 211 shown in FIG. 4 are connected to a conduit 213 that extends to a boiler B. An engine 215 powers the apparatus U and emits waste heat that is preferably recovered by a heat exchanger 217 and utilized in conjunction with boiler B to transform water to steam.

A number of storage reservoirs 219 for liquid reagents have discharge conduits 221 extending therefrom to the intake to a blender 223. Discharge conduits 221 include control valves 221a. A power driven high pressure pump G has the inlet thereof connected by a conduit 225 that has a control valve 225a and check valve 225b therein to the discharge of blender 223. A water supply reservoir 227 has a conduit 229 extending therefrom to the conduit 225. Water conduit 229 has a control valve 229a and check valve 229b therein. Pump G has a conduit 231 extending from the discharge thereof that is connected to the steam supply lines 211 as well as to the conduits 240 and 242 shown in FIG. 9. Flow of liquid through conduit 242 to conduit 232 and nozzles 234 is controlled by a valve 242a. A valve 240a shown in FIG. 9 controls flow of liquid to conduits 236 and nozzles 238. Conduit 231 has a check valve 231a therein.

Figure 17:
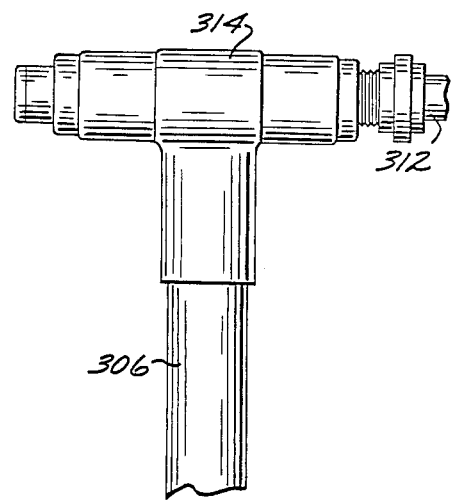
FIG. 17 is an enlarged side elevational view of one of the sampling devices.
Figure 15:
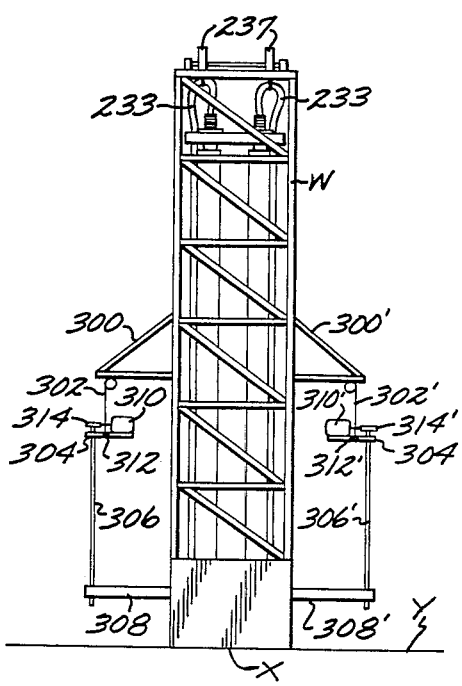
FIGS. 15 and 16 are side elevational views of tha apparatus shown in FIG. 1 modified to include equipment for sampling stations in the hazardous waste impoundment that are to be tested and have been tested.
Figure 16:
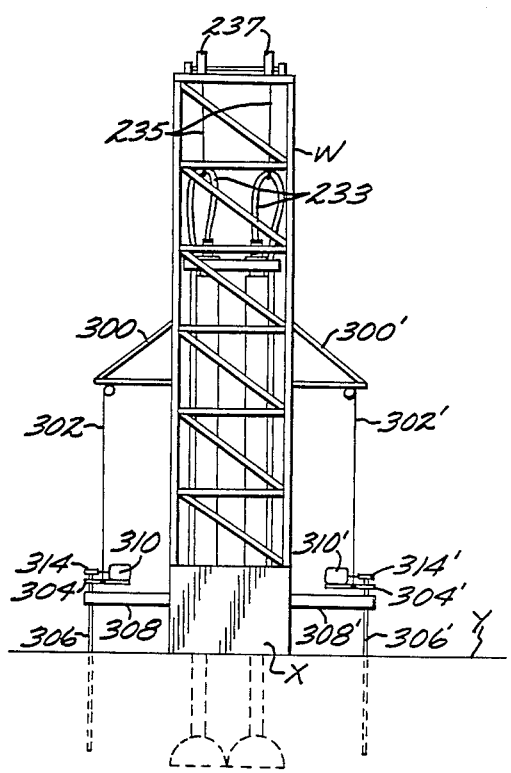

The swivels 180 shown in FIGS. 4 and 5 are connected to pliable hoses 233 that extend upwardly in frame W as shown in FIGS. 16 and 17. The portions of the hoses 233 connected to swivels 180 are in a looped configuration and supported by cables 235 shown in FIGS. 16 and 17 that extend downwardly from spring loaded reels 237 mounted on the upper platform 108 of frame W.

A storage reservoir 239 for dry powdered reactants is provided that is connected by a conduit 241 to the inlet of a feeder H, which feeder is illustrated as being activated to discharge powdered reactants therefrom through a conduit 243 when pressurized air is supplied to the feeder through a conduit 247a that extends to the discharge of an air compressor 247. Conduit 243 is connected to hoses 233.

A conduit 245 extends from the upper part of shroud X to the intake of a power driven blower C, with the discharge of blower C being connected by a conduit 247 to the inlet of a unit P as shown in FIG. 5 that may be either a plasma oven or a catalyst actuated thermal oxidizer, the use of which will later be explained.

The apparatus U is used by moving it to a first station on the toxic waste impoundment Y and thereafter moving the frame W downwardly to force the lower edge 249 of shroud X into sealing engagement with the upper surface of the impoundment Y. The cutters Z are now caused to rotate and are moved downwardly into the impoundment, with the downward movement forming a zone A of particled toxic waste material below the shroud X that extends to a desired depth. The particled material in zone A will be a mixture of hazardous waste and soil.

Continued rotation of cutters Z and vertical movement thereof in zone A maintains the particled material in zone A in an agitated condition. During the formation of the particled material in zone A as well as thereafter, valve 213a in steam supply line 213 is opened and pressurized jets of steam discharge from the nozzles 205 to impinge on the particles and tend to reduce them in size. The steam in addition to serving this function serves to heat zone A, with toxic organic compounds volatile at the temperature of the steam being used being transformed to toxic vapors that rise upwardly through the zone A to flow into the confined space 251 within shroud X. The selection of the temperature and pressure of the steam employed is not critical, so long as the temperature is high enough to ensure that the steam does not condense before it is discharged from nozzles 205, and the pressure is not so great as to prevent a negative pressure from being maintained in the confined space. Steam discharging from nozzles 205 that does not condense flows upwardly in zone A and in so doing tends to displace free toxic gases from zone A, which gases flow upwardly into confined space 251. By actuating pump G and opening valve 229a when steam control valve 213a is closed jets of pressurized water may be caused to discharge from nozzles 234 and 238 to assist cutters Z in forming zone A.

Steam, toxic gases, toxic vapors and air are continuously withdrawn from confined space 251 as a toxic steam by blower C through conduit 245 and discharged to unit P through conduit 245a. The toxic stream is withdrawn from confined space 251 at a sufficiently rapid rate as to maintain a negative pressure therein to preclude the possibility of toxic gases or vapors escaping from confined space 251 to the ambient atmosphere to contaminate the latter.

The sensing unit F later to be described indicates the identity and quantity of toxic compounds present in zone A.

When sensing unit F indicates that toxic hydrocarbons are present in zone A that are not volatile at the temperature of the steam being used, pump G is actuated, and valve 225b opened. Reservoirs 219 contain different liquid reagents that are useful in treating different toxic components that are identified by the sensing unit F. For instance, an aqueous solution of an oxidant such as potassium permanganate may be discharged through nozzles 205 into zone A. For reasons not understood, the potassium permanganate tends to react with long chain hydrocarbons present in zone A to transform them into shorter chain hydrocarbons that are volatile at the temperature of the steam being used and that flow upwardly into confined space 251 as toxic vapors. The potassium permanganate reacts with disagreeable odor forming compounds in zone A such as hydrogen sulphide, sulphur dioxide, mercaptans, chlorinated hydrocarbons present in zone A to transform them into components free of odor.

Dry powdered reactants from the storage reservoir 239 may be discharged into zone A through the second nozzles 202 shown in FIG. 4 by activating compressor 247 to discharge powder from feeder H to conduits 243 and 233. When sensing unit F indicates water soluble salts of toxic metals are present in zone A, powdered calcium oxide may be discharged into the zone by use of feeder H to raise the pH of the toxic waste material therein to the extent that the major portions of the toxic salts are transformed to substantially water insoluble compounds.

The unit P, irrespective to whether it is a plasma oven or thermal catalytic converter, breaks down toxic organic compounds discharged therein into non toxic elements such as hydrogen, oxygen, carbon, carbon dioxide and water that exhaust from unit P through conduit 255. If a portion of the toxic organic components entering unit P are chlorinated hydrocarbons, chlorine released from the break down of the latter will tend to combine with hydrogen that has been released in the break down to form hydrogen chloride.

The conduit 255 is connected to a normally closed pressure relief valve 257 that has a conduit 259 extending therefrom to a hollow vessel 261 containing activated carbon 265. A vent 263 extends from the interior of vessel 261 to the atmosphere. Should excessive pressure build up in conduit 255 it will be relieved by opening of valve 257.

A conduit 267 extends from a junction point 255a to a hydrogen chloride and chlorine removing device 269, which may be either a tower filled with particled iron or magnesium (not shown) or a tower in which the incoming flow of gases is washed with water sprays (not shown) to remove hydrogen chloride and chlorine therefrom.

The gases from unit 269 that are free of hydrogen chloride flow through a conduit 271 to hoses 233 and then downwardly through tubular kellys 164 to discharge back into zone A through second nozzles 202 shown in FIG. 4. It is desirable that hydrogen chloride and chlorine be removed from the gases discharged back into zone A, as at the elevated temperature in the Zone A any chlorine or hydrogen chloride would tend to form chlorinated hydrocarbons with organic compounds remaining in the zone.

The sensing unit F permits the components in the toxic stream to be sampled prior to it entering the unit P and after the stream has been treated and discharges from the unit 269. Sensing unit F includes an organic analyzer 273, inorganic analyzer 275 and recorder 277. The organic analyzer 273 has two inlets 273a and 273b and inorganic analyzer 275 has two inlets 275a and 275b. An instrument line 279 is connected to conduit 271 at junction point 271a and extends into the inlet of a combined pump and refrigeration unit 281 that cools the hot gases, and discharges the cooled gases to a conduit 283 that has a check valve 283c therein and ties into conduit 213. By closing valves 283a and 283b samples of the cooled gases flow to organic analyzer 273 and inorganic analyzer 275 to ascertain that the gases discharging from unit 269 are free of reactive components.

A conduit 285 is connected to a junction point 247a in conduit 247 upstream from unit P and develops into two conduits 287 and 289 that are connected to valves 287a and 289a which when closed place inlets 273b and 275b in communication with water conduit 285 to permit the identity of inorganic toxic components in the toxic stream to be determined prior to the toxic stream being treated by unit P. The sensing unit F also includes instrumentation 291 that indicates pH, ORP and temperature of the material being treated in zone A from probes 293 within shroud X through conduits 295.

When the sensing unit F indicates that the material being treated in zone A has been detoxified to a desired degree, one or more powdered reactants that act as dewatering agents are added thereto from storage reservoirs 239. The storage reservoirs may contain fly ash, calcium oxide, calcium hydroxide, portland cement and powdered long chain hydrocarbon polymers.

When fly ash and portland cement are caused to discharge into zone A through hoses 233 and second nozzles 202, they effect an ion exchange dewatering reaction with clay that is mixed with the detoxified material remaining in zone A, or if that clay is insufficient in quantity, clay is added thereto, with the material in zone A transforming to a hard water impermeable mass. Water soluble salts of toxic metals that have not transformed to substantially water insoluble compounds are enveloped in the hard water impermeable mass and will not leach therefrom, and this is also true of any toxic organic compounds that remain in zone A.

Air discharging from the hydrogen chloride remover 269 throuh conduits 271 and 233 to zone A is prevented from flowing into feeder H due to a check valve 243a in conduit 243. Flow of air to refrigeration unit 281 is controlled by a valve 279a in conduit 279. Conduit 240 shown in FIG. 4 through which liquid is supplied to nozzles 238 is connected to conduit 213 in the same manner as conduits 242.

In summary, the apparatus U and the supporting equipment shown in FIG. 5 are moved to first station adjacent a hazardous waste impoundment Y and the framework W lowered to force the lower edge of the shroud X in sealing engagement with the upper surface of the impoundment. Cutters Z are now rotated and moved downwardly to form a vertically extending zone A of particled hazardous waste that is mixed with soil, and the cutters continue to be rotated and moved longitudinally in the zone to maintain the particled material therein in an agitated state. Pressurized jets of water may be discharged into the agitating particles from the nozzles 234 and 238 and pressurized jets of steam are discharged from the nozzles 205 shown in FIG. 4. The jets of steam impinge on the particles of hazardous waste and tend to reduce the size thereof. The jets of high pressure water create a turbulent mass in the upper portion of zone A. The action of the pressurized jets of steam and water as well as agitating of the particles results in any free toxic gas in zone flowing upwardly therein into the confined space 251 within shroud X. The jets of steam heat zone A and toxic organic compounds volatile at the temperature of the steam being used are transformed to toxic vapors that likewise flow upwardly in zone A into confined space 251. Blower C operates continuously to withdraw a toxic stream that includes air, steam, toxic gases and toxic vapors from the confined space 251 at a sufficiently rapid rate as to maintain a negative pressure in confined space 251 and in so doing eliminating the possibility of toxic vapors or gases leaking from shroud X to contaminate the ambient atmosphere. To achieve such a negative pressure it is necessary that the volume of the toxic stream withdrawn from confined space 251 be greater than the volume of the stream recycled back to the confined space. To that end a cooling tower 520 is provided that has an inlet 520a and outlet 520b. A valve 522 is provided in conduit 271. A conduit 524 extends from conduit 271 upstream from valve 522 to inlet 520a and a conduit 526 connects outlet 520b to conduit 271 downstream from valve 522. Conduit 524 has a valve 524a therein. By closing valve 522 and opening valve 524a the cooling tower 520 condenses steam in the stream flowing back to zone A through conduit 271. The recycled stream is of less volume than the volume of the toxic stream withdrawn from shroud X by blower C, and as a result a negative pressure is maintained in the shroud.

The pressurized toxic stream is discharged from blower C and by unit P is freed of toxic components and thereafter is directed through unit 269 to have any hydrogen chloride or chlorine removed therefrom after which the stream is recycled back into zone A as above described to displace toxic gases and vapors remaining therein upwardly into confined space 251.

Sampling of the identity and quantity of toxic components in zone A and in the toxic stream is carried out by a sensing unit F. When sensing unit F indicates the presence of toxic hydrocarbons in zone A that are not volatile at the temperature of the steam being used, or disagreeable odor producing compounds such as hydrogen sulphide, sulphur dioxide, mercaptans, chlorinated hydrocarbons are present, pump G is actuated to discharge an appropriate liquid oxidizing agent into zone A. An aqueous solution of potassium permanganate has been found satisfactory for this purpose, as it not only eliminates undesirable odors but for reasons not understood reacts with long chain toxic hydrocarbons not volatile at the temperature of the steam being used to transform a substantial portion thereof to shorter chain hydrocarbons that are volatile and flow upwardly as toxic vapors into confined space 251.

If sensing unit F indicates the presence of water soluble salts of toxic metals in zone A, the dry reagent feeder H is actuated to discharge a dry material downwardly through the tubular kellys 164, tubes 176 and 178, and second nozzles 202 into zone A. By the time such material is added, the particles of toxic waste and soil have in most instances transformed to a flowable pasty mass due to agitation thereof and the action of steam and water thereon. When a powdered material such as calcium oxide is added in an amount sufficient to raise the pH of the material in zone A to substantially 11, the soluble salts of most toxic metals will be precipitated as substantially water insoluble compounds.

After sensing unit F indicates that zone A has been detoxified to a desired degree feeder H is actuated to discharge a dewatering agent into zone A, such as a mixture of fly ash and portland cement. This mixture effects an ion exchange with clay present in zone A, and the material in the zone transforms to a hard impermeable mass of substantial density. The cutters Z are withdrawn from zone A prior to this transformation being effected. Should radioactive material be present in zone A, little or no radon gas will be emitted from the treated zone. The material in the treated zone is sufficiently dense that prior to the time radon would have escaped therefrom the radon would have transformed to a solid radioactive material. The last mentioned material, as well as toxic hydrocarbons that have not been removed from zone A, as well as water soluble salts of toxic metals that have not transformed to substantially water insoluble compounds remain enveloped in the transformed water impermeable material in zone A and will not leach therefrom.

After the detoxification has been completed at a first station the apparatus U and the supporting equipment shown in FIG. 5 is moved to a succession of overlapping second stations where the above described method is repeated.

The insitu detoxifying method carried out by the apparatus W may be varied. For instance after zone A has had the toxic organic compounds voltaile at the temperature of the steam being used removed therefrom, micro-organisms of a type already present in the impoundment or that have been genetically engineered to biodegrade the hazardous waste are introduced into the zone with a liquid nutrient after the zone has cooled. Such introduction is by use of pump G. The cutters Z are now withdrawn and the apparatus U moved to a second station where the method is repeated. The micro-organisms will over a period of time biodegrade the zone in which they are placed. After the micro-organisms have been implanted in zone A as above described they must periodically be furnished a nutriment.

Due to the random distribution of hazardous waste in an impoundment, it is desirable that the toxic components in the zone at the next second station be determined while the insitu detoxification at a first station is underway. Also, it is desirable that a zone that has just been treated be subjected to verification that the desired quantity of toxic components has been removed therefrom.

Two supports 300 and 300' extend outwardly from opposite sides of framework W and by spring loaded cables 302 and 302' or other conventional means support two drill assemblies 304 and 304' that impart sonic vibrations to two hollow drill rods 306 and 306'. Drill rods 306 and 306' extend downwardly through vertical openings (not shown) in two horizontal guides 308 and 308' that are secured to framework W. Each drill assembly 304 and 304' includes an engine 310 that through a conductor 312 imparts sonic vibrations to a head 314 that transfers the vibrations to drill rod 306. Vibration of the drill rods 306 and 306' causes them to move downwardly in impoundment Y as shown in FIG. 17 to secure cores thereof (not shown) that are subsequently checked as to the toxic components therein by use of sensing unit F or by other appropriate analyzing means. Drilling equipment as above described is commercially available through Condor Earth Technologies, P.O. Box 4249, Modesto, Calif.

Figure 7:
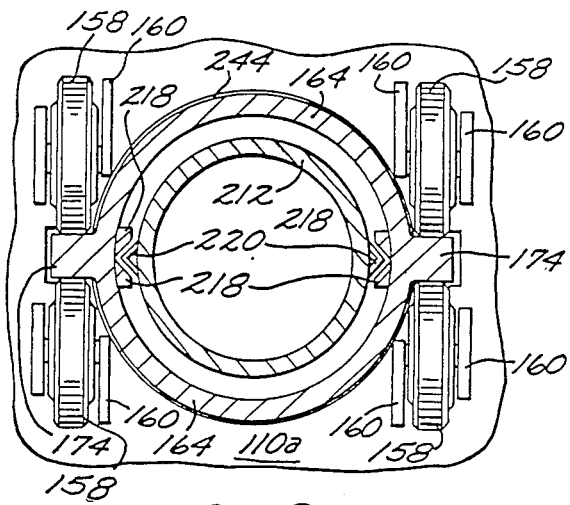
FIG. 7 is a modification of the portion of the assembly shown in FIG. 1 that is used in determining and verifying the identity and quantity of toxic contaminants in a hazardous waste impoundment.

The first form of movable assembly J shown in FIG. 1 may be modified as illustrated in FIG. 7 to an assembly J-1 that is used in verifying the location of various portions of toxic waste that is randomly distributed in an impoundment Y and the identity of the toxic waste at each location. Such verification is necessary, for many toxic waste impoundments are relatively old, and records in many instances as to the identity of the toxic waste and the location thereof in the impoundment is either not available or incomplete.

The verifier assembly J-1 differs from the first assembly J as may be seen in FIG. 7 by including but a single kelly 164 and cutter Z-1, which cutter includes a core forming and retrieving structure 320 of a type commercially available for use in oil fields and that need not be described in detail. The single cutter Z-1 forms a downwardly extending zone A-1 in the same manner as previously described with zone A and the sensing unit F provides information as to the identity of toxic components in the zone A-1 and the quantity thereof. Zones A-1 are formed at selected stations on the impoundment Y to provide information that will be of assistance in the subsequent detoxification of the impoundment.

In industry, hazardous toxic waste may accumulate above ground in stock piles or be newly formed, and frequently contains high concentrations of both toxic organic compounds and water soluble salts of toxic metals. Illustrations of such hazardous toxic waste are accumulations of oil well drilling mud, metal treating materials, residues from pesticide manufacture, paint residues, wastes from chemical manufacture, contaminated wash water and the like. Such toxic materials may be in the form of liquids, slurries or solids. The hauling of such toxic waste over public highways to a dump site is hazardous, in that, the contaminated waste may be inadvertently spilled if in the form of liquids and slurries, and dust and out gassing from the material may contaminate the ambient atmosphere if it is in solid form.

Figure 13:
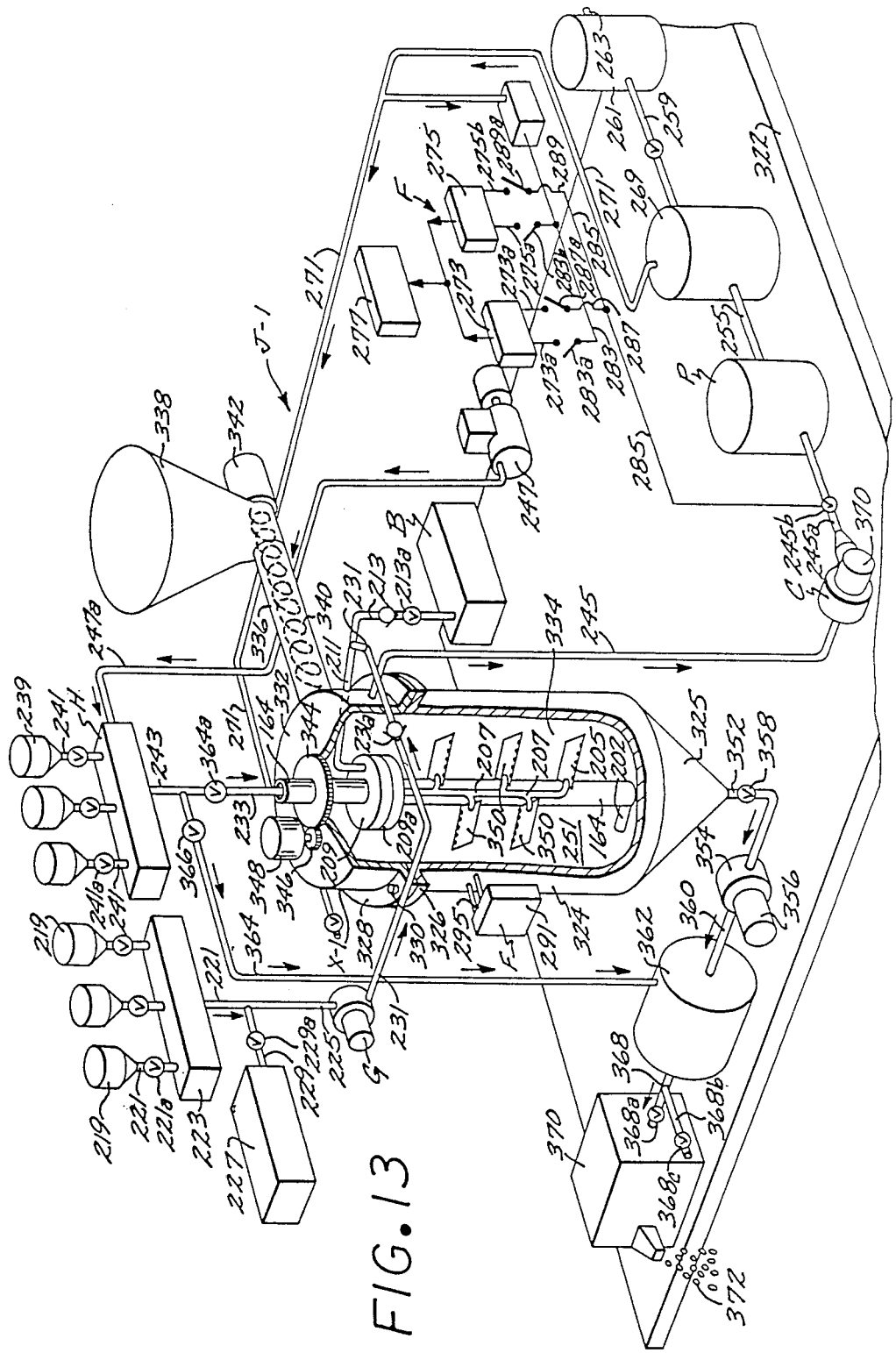
FIG. 13 is a diagrammatic perspective view of a first form of assembly that is mounted on a base and may be disposed adjacent a stockpile of above ground hazardous waste to detoxify the latter.
Figure 14:
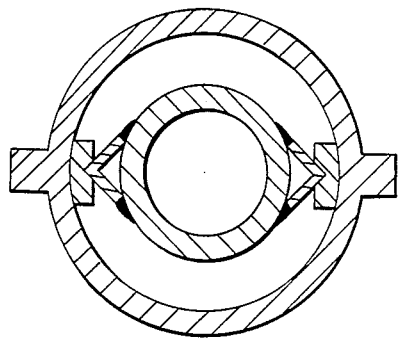
FIG. 14 is a transverse cross sectional view taken on the line 14—14 of FIG. 4.

In FIG. 13 a diagrammatic perspective view of an assembly M is shown in which the apparatus illustrated in FIGS. 1 and 5 is modified to be mounted on a base 322, and the assembly M capable of being transported to an above ground site of hazardous waste for the insitu detoxification of the latter.

In the assembly M shown in FIG. 13 elements common to the apparatus illustrated in FIG. 1 and 5 are identified by the numerals and letters previously used. In FIG. 13 it will be seen that the assembly M includes an elongate vertically extending vessel 324 that has an open top that is illustrated as defined by a ring shaped flange 326. A shroud X-1 in the form of an inverted cup shaped member having a ring shaped flange 328 is removably and sealingly secured to flange 326 by bolts 330 or other suitable fastening means. Shroud X-1 is shown as having a flat upper top 332. The lower end portion 334 of vessel 324 is shown as being of downwardly and inwardly extending configuration 325.

A tubular kelly 164 extends downwardly and sealingly through an opening (not shown) in top 332 into the interior confined space 334 of the vessel, which interior corresponds to the zone A, in that, the toxic material to be treated is disposed therein.

A tubular member 336 extends outwardly from the upper portion of vessel 324 and has an upwardly extending hopper 338 on the outer end thereof into which the hazardous waste is fed. A screw conveyor 340 is rotatably supported in tubular member 336 and is driven by a motor 342. As the screw conveyor 340 rotates, toxic waste (not shown) from hopper 338 is fed into the confined space 334.

Kelly 164 has a gear 344 secured to the upper portion thereof above top 332 that is driven by a gear 346 that is rotated by a motor 348. A number of vertically spaced horizontal blades 350 extend outwardly from kelly 164 in the interior confined space 334 and correspond to cutters Z in that they have nozzles 205 on the trailing edges thereof through which pressurized jets of steam are discharged.

Steam is supplied to nozzles 205 through passages (not shown) in the blades 350 that are in communication with a conduit 207 that extends upwardly to a hollow rotary swivel 209 supported on kelly 164 as previously described, and that has a steam supply conduit 211 in communication therewith. The upper portion 209b of swivel 209 remains stationary and the lower portion 209a rotates with kelly 164.

The lower vessel portion 325 has a conduit 352 extending therefrom to the inlet of a pump 354 that is driven by a motor 356. A valve 358 controls flow of material through conduit 352. A discharge conduit 360 extends from pump 354 to the inlet of a power driven mixing device 362 such as a muller or the like. A conduit 364 extends from conduit 243 to the interior of mixing device 362 to permit the discharge of a dry chemical thereinto from the feeder H when compressor 247 is actuated, valve 364a is closed, and valve 366 is in an open position. Treated and detoxified waste is discharged from mixing device 362 through a conduit 368 to a pellet forming device 370 that discharges pellets 372 therefrom. Conduit 368 has a valve 368a therein. A discharge conduit 368b extends outwardly from conduit 368 upstream from valve 368a and has a valve 368c therein. By closing valve 368a and opening valve 368c detoxified material may be discharged from mixing device 362 without being formed into pellets 372.

The assembly J above described may be operated on a batch basis or continuously at the election of the user. When operating on a batch basis, motor 342 is actuated to rotate conveyor 340 to discharge toxic waste from hopper 338 into confined space 334 until vessel 324 is filled up to approximately flange 326. Motor 348 is actuated to rotate kelly 164 and blades 350. Valve 213a is opened to discharge steam from nozzles 205 to heat the toxic waste in confined space 334 to displace free toxic gases therefrom and cause toxic organic compounds that are volatile at the temperature of the steam being used to transform to toxic vapors that flow upwardly into confined space 251 of shroud X-1. A motor 370 that drives blower C is actuated to cause the blower to withdraw a toxic stream of air, steam, toxic gases and toxic vapors from confined space 251 and discharge them through conduit 245a, unit P, conduit 255, unit 269, conduit 271, and conduit 233. The steam by the time it reaches conduit 233 is free of toxic components and thereafter discharges into confined space 334 from nozzle 202. Dry chemicals, liquid chemicals and water may be added to toxic waste in confined space 334 by use of pump G and air compressor 247 in the same manner and for the same purposes as previously described in operation of the assembly J shown in FIG. 5.

When sensing unit F indicates that the material in confined space 334 has been detoxified to a desired degree, valve 358 is opened and pump 354 activated to discharge the material to mixing device 362 where it is mixed with a dry chemical such as a dewatering agent that is discharged into the mixing device through conduit 364. The material mixed with the dewatering agent will solidify to a water impermeable mass but before so doing it is discharged to unit 370 to be formed into pellets 372 or bodies of other desired shape that can be transported to a desired destination without contaminating the ambient atmosphere or the landscape should they inadvertently be spilled. The detoxified material may also be discharged through conduit 360b without being formed into pellets. The assembly J-1 above described is particularly useful in treating drilling mud that is contaminated with various hydrocarbons such as produced on off shore oil well sites and drilling platforms. A relief valve 374 is provided that is normally closed but opens to relieve the negative pressure that occurs when treated material is withdrawn from confined space 334.

When the assembly J operates continuously the same method as above described is followed, but the flow of toxic waste into confined space 334 must be at such a rate that it is detoxified prior to being withdrawn through the conduit 352. When operating continuously the pump 354 must be capable of creating a suction of greater magnitude than the negative pressure created by blower C.

The second form of assembly K shown in FIG. 6 accomplishes the same results as first assembly J, but differs from the latter by actually removing toxic components from the toxic stream rather than transforming them to non-toxic components and hydrogen chloride and chlorine.

Elements in assembly K common to elements previously identified by numerals and letters in assembly J continue to be identified by the same numerals and letters but with primes added thereto.

The second assembly K shown in FIG. 6 is used in the same manner and produces the same results as first assembly. Second assembly K differs primarily from the first assembly J in the manner by which toxic components are separated from the toxic stream from blower C', and the additional feature of using a plasma oven to regenerate used activated carbon.

In the use of second assembly K the cutters Z' are rotated and moved downwardly to form a zone A' of particled waste from the impoundment Y', and the cutters continuing to be rotated to maintain the particled material in an agitated condition. By actuating pump G', opening valve 229a', water can be discharged into zone A' through nozzles 205' and by opening valve 242' water can also be discharged through nozzles 234'. After a desired amount of water is added to zone A' the above procedure is reversed.

By opening value 213a' steam is caused to flow from boiler B' to discharge from nozzles 205' for the reasons previously described in the operation of assembly J. Blower C' is actuated to withdraw a toxic stream from confined space 251' at a sufficiently rapid rate as to maintain a negative pressure therein. The toxic stream is discharged through conduit 245a' and flows in succession through a number of refrigerating units 400, 402 and 404 that produce increasingly lower temperatures and are connected by conduits 406. The stream discharges from refrigerating unit 404 through a conduit 408 to a reheat unit 414 that is heated by steam that flows thereto through a conduit 410 that has a flow control valve 412 therein.

Refrigerating unit 400 is at a sufficiently low temperature as to condense steam to water. Refrigerating units 402 and 404 are at sufficiently low temperatures as to condense toxic organic vapors to liquids. The steam condensate and condensed toxic organic liquids flow by gravity through a conduit system 413 to a residue receiving tank 416. A drain conduit 418 extends to both a bio-reactor 420 and catalyst actuated thermal oxidizer 422, with the flow thereto being controlled by valves 424 and 426. Fumes from bio-reactor 420 and thermal oxidizer 422 flow through a conduit assembly 428 to confined space 251'. Conduit assembly 428 has a check valve 430 therein.

The stream discharges from the reheat unit 414 through a conduit 434 to a toxic gas adsorbing unit 436 that contains activated carbon 438. The stream discharging from unit 436 flows through conduit 440 that when a normally closed emergency valve 442 is opened discharges the stream to the ambient atmosphere. When valve 442 is in a normally closed position, the stream discharges through a conduit 444 back to the intake of air compressor 247'. The pressurized stream from compressor 247' flows through conduit 247a' to the intake of a heater 446, with the heated pressurized stream from heater 446 flowing through a conduit 448 to conduit 243' to subsequently discharge into confined space 251' through nozzles 202'. Conduit 448 has a control valve 450 therein. Heat is supplied to heater 446 by steam that flows thereto through a conduit 452 that is connected to conduit 213'. Due to the above described recycling of the toxic stream back to confined space 251' as a detoxified air stream no toxic pollutants can escape to the ambient atmosphere during the detoxification of zone A'.

Liquid reagents and dry powdered chemicals can be discharged when desired into zone A' by manipulation of valves as previously described in connection with the operation of assembly J.

Conduit 247a' is also connected to the intake of dry feeder H', and by opening a valve 452 the feeder may be actuated. A by-pass conduit 454 extends from conduit 434 from a position up stream from a valve 456 in the latter to conduit 444 up stream from a check valve 458 in the latter. Conduit 454 has a valve 460 therein which when opened permits the stream discharging from reheat unit 414 to flow back to confined space 251' without flowing through unit 436.

Instrumentation lines 462 and 464 and line assemblies 466 with valves 468, 470 and 472 permit identification of and the quantity of toxic components in the toxic stream after initial cooling by refrigeration unit 400 and after it has flowed through reheat unit 414. Electric signals are transmitted through conductors 474 to recorder 277'.

Activated carbon 438 that has been used is transmitted by a suitable conductor 480 to thermal oxidizer 422 where it is heated to a sufficiently high temperature as to be regenerated, and regenerated activated carbon discharging to a suitable container 482 through conduit 484 and residue through a conduit 486 to container 488. Upon completion of the insitu detoxifying of a zone A' at a first station, the assembly K is moved to a second station to repeat the operation.

In addition to the detoxification previously described, the apparatus U may be used to vitrify zone A if the same is of a sandy or clay composition. Such vitrification is accomplished by the use of plasma torches 550 held in the lower ends of tubes 196 by supports 552 as shown in FIG. 12. After the zone A has been particled by use of cutters Z, the cutters are moved upwardly therein and the material therebelow is subjected to plasma arcs to melt, and the melted material subsequently cooling to a vitrified, water insoluble, rigid mass. In the event the hazardous waste in zone A does not contain sufficient sand or clay to vitrify, sand, clay or other vitrifiable material is added thereto through kellys 164 by an air stream during the forming of the hazardous waste into particles.

The use and operation of the invention has been described previously in detail and need not be repeated.

I claim:

1. A method for detoxifying in situ a desired portion of hazardous toxic waste to a desired degree without contaminating the ambient atmosphere, which method includes the steps of:
   (a) defining a confined space in sealing communication with said desired portion that extends upwardly thereabove:
   (b) agitating said desired portion;
   (c) discharging pressurized steam into said desired portion to transform toxic organic compounds into toxic vapors that, together with free toxic gases that may be present in said desired portion, flow upwardly into said confined space above said desired portion;
   (d) withdrawing air, steam, toxic vapors and toxic gases from said confined space above said desired portion as a toxic stream at a sufficiently rapid rate as to maintain a negative pressure in said confined space to prevent toxic materials in said confined space from leaking therefrom to contaminate the ambient atmosphere;
   (e) pressurizing said toxic stream;
   (f) freeing said pressurized toxic stream of toxic components and steam and recycling the resulting pressurized stream back to said desired portion;
   (g) sensing the identity and quantity of toxic components in said confined space; components in said confined space;
   (h) discharging an oxidizing agent into said desired portion when said sensing indicates the presence of a disagreeable odor producing organic compound therein or a water soluble salt of a toxic metal to transform said odor producing organic compounds to non-odor producing compounds and the major portion of said water soluble salts of toxic metals to substantially water insoluble compounds;
   (i) discharging a dewatering agent into said desired portion after said sensing indicates that desired portion has been detoxified to a desired degree to solidify said desired portion into a water insoluble mass from which toxic organic compounds and water soluble salts of toxic metals that have not been transformed to water insoluble compounds will not leach out; and
   (j) terminating said agitating prior to said solidification.

2. The method as defined in claim 1 which includes the additional step of:
   (k) forming said desired portion to which said dewatering agent has been added into a plurality of pellets prior to said solidification being completed.

3. The method as defined in claim 1 in which said desired portion contains vitrifiable material, including the further step of subjecting said desired portion to the action of a plasma torch to transform the latter into a vitrified mass.

4. The method of claim 1 further comprising the step
   (k) moving said confined space from a first station at which said steps are performed to a second station overlapping said first station and repeating said method of detoxifying in situ, and so continuing until all desired portions of toxic waste material have been detoxified to the desired extent.

5. The method of claim 1, wherein said dewatering agent is alkaline and is discharged into said desired portion in an amount not only sufficient to solidifying said desired portion into said water impermeable mass but to raise the pH of water in said waste material prior to said solidification to the extent that water soluble salts of toxic metals are precipitated as substantially water insoluble compounds and those water soluble salts of toxic metals not so precipitated remain enveloped in said water impermeable mass from which they will not leach out in toxic quantities.

6. The method of claim 1 in which said toxic waste contains a radon emitting radioactive material and said dewatering agent is added in an amount sufficient to transform said desired portion into a solid water impermeable mass of such density that the migration of radon therethrough is sufficiently slow that said radon transforms to a solid radioactive isotope during said migration and does not escape to the ambient atmosphere and said radioactive isotope remaining in said water impermeable mass from which it will not leach out in toxic quantities.

7. The method of claim 1, in which said waste is mixed with soil which includes a substantial quantity of a sodium containing clay, and said dewatering agent contains calcium that enters into an ion exchange with said sodium in said clay to transform said desired portion from a hydrophilic condition to a hydrophobic solid water impermeable mass.

8. The method of claim 1, in which said dewatering agent includes dry sodium containing clay and a calcium containing compound which when dissolved by water in said toxic waste material and soil effects an ion exchange of said sodium and calcium and in so doing transforms said desired portion from a hydrophilic state to a hydrophobic solid water impermeable state.

9. The method claim 1, in which said oxidizing agent tends to transform long chain hydrocarbons that are not volatilized by said steam into shorter chain hydrocarbons that are volatilized by said steam and flow upwardly as vapors into said confined space.

10. The method of claim 9, wherein said oxidizing agent is potassium permanganate.

11. The method of claim 1, in which said toxic waste material is agitated by the vertical movement of at least one substantially horizontal rotating cutting blade that is rotated by power from a waste heat emitting engine, and said method including the further steps of:
    (k) providing a stream of water from a source thereof to a heat exchanger heated at least in part by said waste heat from said engine; and
    (l) discharging said stream of water through said heat exchanger to be transformed to steam that is discharged upwardly through said waste material.

12. The method of claim 1, in which the step of freeing said toxic stream of toxic components and steam include:
    (k) subjecting said toxic stream to a plurality of increasingly lower temperatures to separate steam from said toxic stream as condensate, and toxic gases and vapors as toxic liquids.

13. The method of claim 12, which includes the further step of:
   (l) discharging toxic components resulting from said toxic stream being subjected to a plurality of increasingly lower temperatures into a closed container; and
   (m) subjecting said toxic components from said container to bacterial action to render them non-toxic.

14. The method of claim 12, which includes the further steps of:
   (l) discharging toxic components resulting from said toxic stream being subjected to a plurality of increasingly lower temperatures into a closed container; and
   (m) subjecting said toxic components from said container to the heat of a plasma furnace to render them non-toxic.

15. The method of claim 1, in which the step of freeing said toxic stream of toxic components and steam includes:
   (k) subjecting said toxic stream to a plurality of increasingly lower temperatures to separate steam from said toxic stream as condensate and toxic gases and vapors as toxic liquids;
   (l) sensing said toxic stream as to the identity and quantity of toxic components in said toxic stream when said toxic stream is subjected to the first of said lower temperatures and the last of said lower temperatures to determine that toxic components in said toxic stream have been removed therefrom to a desired degree; and
   (m) subjecting said toxic stream after being cooled to the last of said lower temperatures to activated carbon to remove substantially all toxic components remaining therein.

16. The method of claim 1, in which said desired portion is a station located on the periphery of a geographic area containing hazardous waste, and further comprising the step of detoxifying overlapping subsequent stations that extend around said periphery resulting in a detoxified, water impermeable, solid hazardous waste containment wall free of windows.

17. The method of claim 1, in which said desired portion is formed by the vertical movement of at least one power driven, substantially horizontal elongate blade that has a cutting edge and a trailing edge, said blade having a plurality of longitudinally spaces openings adjacent said trailing edge, and said stream of steam being discharged through said plurality of openings into said desired portion as a plurality of high pressure jets that impinge on particles of hazardous waste material formed by said cutting blade to reduce the size of said particles to encourage the escape of free toxic gases therefrom and increase the surface area of said hazardous waste material exposed to said oxidizing agent.

18. An apparatus for detoxifying a desired portion of hazardous toxic waste to a desired degree, without contaminating the ambient atmosphere, said hazardous toxic waste being one that may contain toxic organic compounds and water soluble salts of toxic metals, said apparatus including:
   (a) confined space defining means in sealing communication with said desired portion and extending thereabove;
   (b) first means for agitating said desired portion;
   (c) second means for discharging pressurized steam into said desired portion to transform toxic organic compounds into toxic vapors which with free toxic gases that may be present in said desired portion flow upwardly into the upper part of said confined space;
   (d) third means for withdrawing air, steam, toxic vapors and toxic gases from the part of said confined space above said desired portion as a toxic stream and at a sufficiently rapid rate as to maintain a negative pressure in said confined space to preclude said toxic gases and vapors leaking from said confined space to contaminate the ambient atmosphere and said third means pressurizing said toxic stream;
   (e) fourth means for freeing said pressurized toxic stream of toxic components and steam;
   (f) fifth means for discharging said pressurized stream free of toxic components back into said desired portion;
   (g) sixth means for sensing the identity and quantity of toxic components in said desired portion;
   (h) seventh means for discharging an oxidizing agent into said desired portion when said sixth means indicates disagreeable odor producing organic compounds or water soluble salts of toxic metals are present in said desired portion to transform said disagreeable odor producing organic compounds to non-odor producing compounds and the major portions of said water soluble salts of toxic metals to substantially water insoluble compounds;
   (i) eighth means for discharging a dewatering agent into said desired portion when said sixth means indicates said desired portion has been detoxified to a desired degree, with said dewatering agent transforming said desired portion to a hard, water impermeable mass after said is terminated, and from which mass toxic components remaining therein will not leach out.

19. An apparatus as defined in claim 18, in which said hazardous toxic waste is underground in an impoundment thereof, with said apparatus being movable from station to station on said impoundment, with said confined space defining means being an inverted cup shaped rigid shroud that has a lower edge and said first means a cutter, said apparatus including:
   (j) ninth means that movably support said shroud and permit said lower edge thereof to be disposed in sealing contact with said impoundment at a desired station thereon; and
   (k) tenth means for rotating said cutter and moving said cutter longitudinally below said shroud to form said desired portion of said hazardous waste impoundment into a downwardly extending zone of particles thereof, said particles after being formed being agitated by continued rotation of said cutter.

20. An apparatus as defined in claim 19, in which each of said cutters includes at least one substantially horizontal blade that has a leading edge and a trailing edge, said apparatus in addition including:
   (l) a plurality of spaced nozzles on the trailing edge of said blade in communication with said second means, with said steam discharging from said nozzles as a plurality of jets that impinge on said particles and tend to reduce the size thereof as well as raise the temperature of said particles.

21. An apparatus as defined in claim 20, in which said fourth means is a power driven blower that has the intake thereof in communication with said confined space in said shroud and the discharge outlet in communication with said fifth means.

22. An apparatus as defined in claim 19, in which said fourth means is a plasma arc oven; a reactive gas remover; and a cooling device through which said toxic stream sequentially flows prior to entering said fifth means, said plasma arc oven transforming toxic vapors and gases in said stream to non-toxic materials, said remover removing reactive gases from said stream, and said cooling device cooling said stream to the extent that steam present therein is transformed to condensate.

23. An apparatus as defined in claim 19, in which said fourth means is a refrigerator and container of activated carbon through which said toxic stream flows in succession prior to entering said fifth means, said refrigerator transforming steam and toxic organic vapors to liquids, and said activated carbon absorbing toxic gases not removed from said stream by said refrigerator.

24. An apparatus as defined in claim 23, which in addition includes:
 (j) a conduit in communication with said refrigerator through which condensed liquids that may contain toxic material flow; and
 (k) tenth means in communication with said conduit that transform toxic material that flows thereinto through said conduit to non-toxic components.

25. An apparatus as defined in claim 24, in which micro-organisms are present in said tenth means to transform said toxic materials to non-toxic components.

26. An apparatus as defined in claim 24, in which said tenth means is a plasma arc oven that transforms said toxic material to non-toxic components, and that regenerates used activated carbon delivered thereto to a usable form.

27. An apparatus as defined in claim 19, in which said space defining means is a closed vessel in which said desired portion is disposed during the detoxification thereof, and said apparatus in addition including:
 (j) ninth means for disposing said desired portion within said closed vessel; and
 (k) tenth means for removing said desired portion from said vessel prior to said desired portion transforming to said water impermeable mass.

28. An apparatus as defined in claim 19, further including:
 (j) means for discharging water into said desired portion to transform said desired portion into a mass of a desired consistency.

29. An apparatus as defined in claim 19, in which said fourth means includes:
 (j) a catalyst actuated thermal oxidizer, reactive gas removing means and a steam condensing means through which said toxic stream flows in succession prior to entering said fifth means, said catalyst actuated thermal oxidizer transforming said toxic vapors and toxic gases to non-toxic compounds.

* * * * *

UNITED STATES PATENT AND TRADEMARK OFFICE
CERTIFICATE OF CORRECTION

PATENT NO. : 4,844,807

DATED : July 4, 1989

INVENTOR(S) : Frank Manchak, Jr.

It is certified that error appears in the above-identified patent and that said Letters Patent is hereby corrected as shown below:

Col. 6, line 67, after "spaced" the following should be inserted

-- teeth 206 on the leading edges thereof. Circular plate 198 is secured to flange 182 by conventional means such as bolts 210 or the like. A number of longitudinally spaced nozzles 205 are supported on the trailing edge portion of one of the blades 204 and are in communication with a passage (not shown) in the blade that is connected to a conduit 207 that extends upwardly to a lower portion 209a of a swivel 209. The lower swivel portion 209a rotates with cutter Z. An upper portion 209b of the swivel 209 is stationary and is so supported by straps 209c that are secured to brackets 209d that extend downwardly from lower platform 110. High pressure steam or liquid is supplied to swivel 209 through a conduit 211 for purposes that will later be explained. In Figure 8 it will be seen that each kelly 164 has two groove defining members 218 secured to the interior surface thereof that slidably engage ribs 220 secured to tube 178.

UNITED STATES PATENT AND TRADEMARK OFFICE
CERTIFICATE OF CORRECTION

PATENT NO. : 4,844,807

DATED : July 4, 1989

INVENTOR(S) : Frank Manchak, Jr.

Figure 9:
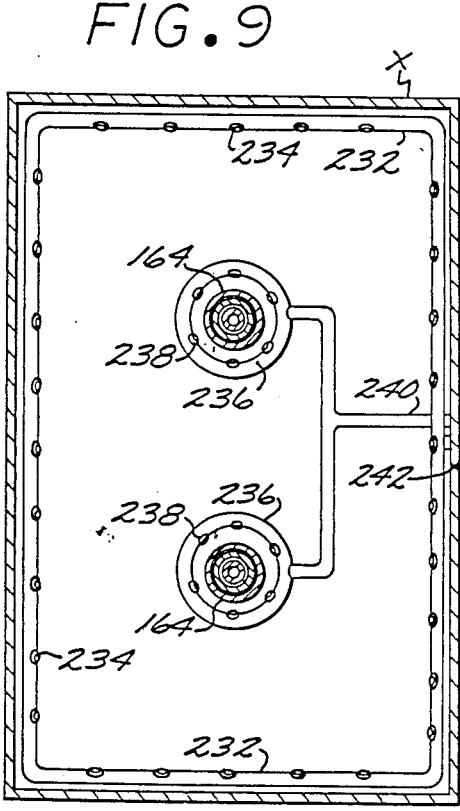
FIG. 9 is a bottom plan view of the assembly shown in FIG. 4 taken on the line 9—9 thereof.

It is certified that error appears in the above-identified patent and that said Letters Patent is hereby corrected as shown below:

In Figures 4 and 9 it will be seen that a tubular rectangular frame 232 is supported from the underside of lower plate 110b within shroud X and has spray nozzles 234 extending outwardly therefrom. Circular tubes 236 are supported from lower plate 110b and extend around kellys 164 and support nozzles 238. Liquid under pressure is supplied to tubular frame 232 by a pipe 240 and to circular tubes 236 by a pipe 242 by equipment later to be described. The liquid supplied to tubular frame 232 and circular tubes 236 may be pressurized or a liquid agent. The water or liquid agent is formed into pressurized --

UNITED STATES PATENT AND TRADEMARK OFFICE
CERTIFICATE OF CORRECTION

PATENT NO. : 4,844,807

DATED : July 4, 1989

INVENTOR(S) : Frank Manchak, Jr.

It is certified that error appears in the above-identified patent and that said Letters Patent is hereby corrected as shown below:

Col. 17, lines 39 and 40, "components in said confined space;" should be deleted.

Signed and Sealed this

Fourteenth Day of January, 1992

Attest:

HARRY F. MANBECK, JR.

*Attesting Officer*     *Commissioner of Patents and Trademarks*